United States Patent [19]

Dunfee

[11] Patent Number: 5,704,904
[45] Date of Patent: Jan. 6, 1998

[54] INFLATABLE LUMBER TRACTION VEST

[75] Inventor: Matthew Dunfee, Jordan, Minn.

[73] Assignee: Antigee Advantage International, Inc., Minneapolis, Minn.

[21] Appl. No.: 806,424

[22] Filed: Feb. 26, 1997

Related U.S. Application Data

[63] Continuation of Ser. No. 474,780, Jun. 7, 1995, abandoned.

[51] Int. Cl.$^6$ ........................................ A61N 1/00
[52] U.S. Cl. ................ 602/13; 602/19; 128/DIG. 20
[58] Field of Search ...................... 128/845, 846, 128/873, 874, 875, 876, DIG. 20; 602/13, 19

[56] References Cited

U.S. PATENT DOCUMENTS

| | | | |
|---|---|---|---|
| 1,589,670 | 6/1926 | Vartia | 602/19 |
| 3,186,405 | 6/1965 | Bailey | 602/13 |
| 3,868,952 | 3/1975 | Hatton | 602/13 |
| 3,993,056 | 11/1976 | Rabischong et al. | |
| 4,269,179 | 5/1981 | Burton et al. | |
| 4,497,517 | 2/1985 | Gmeiner et al. | |
| 4,552,135 | 11/1985 | Racz et al. | |
| 4,559,933 | 12/1985 | Batard | 602/13 |
| 4,622,957 | 11/1986 | Curlee | |
| 4,624,248 | 11/1986 | Poole et al. | |
| 4,682,588 | 7/1987 | Curlee | |
| 4,685,668 | 8/1987 | Newlin, Jr. | |
| 4,691,696 | 9/1987 | Fanfan de los Godos | |
| 4,702,235 | 10/1987 | Hong | |
| 4,768,499 | 9/1988 | Kemp | |
| 4,898,185 | 2/1990 | Fuller | |
| 4,960,115 | 10/1990 | Runciato | 128/DIG. 20 |
| 4,991,572 | 2/1991 | Chases | |
| 4,991,573 | 2/1991 | Miller | |
| 5,060,639 | 10/1991 | Marcus | |
| 5,062,414 | 11/1991 | Grim | |
| 5,076,264 | 12/1991 | Lonardo et al. | |
| 5,101,815 | 4/1992 | Lungdon-Orr | 128/DIG. 20 |
| 5,111,807 | 5/1992 | Spahn et al. | |
| 5,135,471 | 8/1992 | Houswerth | |
| 5,188,586 | 2/1993 | Castel et al. | |
| 5,256,135 | 10/1993 | Avihod | |
| 5,338,289 | 8/1994 | Cooker | |
| 5,382,266 | 1/1995 | Graham | |
| 5,403,266 | 4/1995 | Bragg et al. | |
| 5,441,479 | 8/1995 | Chitwood | |

OTHER PUBLICATIONS

AliMed Catalog 1993, p. 28.
Flaghouse Rehab Catalog 1993, p. 39.
The Saunders Group, Inc. Catalog, p. 37.

Primary Examiner—Michael A. Brown
Attorney, Agent, or Firm—Patterson & Keough, P.A.

[57] ABSTRACT

Disclosed herein is an inflatable lumbar traction vest capable of both preventing spinal injuries, and facilitating the healing of existing spinal injuries. As disclosed, the vest of the present invention comprises an upper torso member, a lower belt member, and a plurality of vertical support members fixedly attached at each end to the upper and lower members, wherein each of the vertical support members contains therein an inflatable bladder in fluid connection to an inflation means.

26 Claims, 3 Drawing Sheets

INFLATABLE LUMBER TRACTION VEST

This is a continuation of application No. 08/474,780, filed Jun. 7, 1995 now abandoned.

FIELD OF THE INVENTION

This invention relates in general to devices to aid in the healing of lower back injuries or to support the lower back to prevent the occurrence of injuries.

BACKGROUND OF THE INVENTION

Since homo sapiens first began to walk upright, man has dealt with the pain, aggravation and loss of productivity arising from spinal injuries, particularly those to the lower back. It is not without good reason that the phrase, "Oh, my aching back!" is a common part of our everyday lexicon. The relative ease with which injuries to the spine and supporting musculature are incurred, as well as the debilitating effects of even slight injuries, merely adds to the overall severity of the problem of dealing with spinal injuries. Further aggravating the situation is that the most frequently prescribed regimen of treatment for spine-related injuries, such as those to the lower back, short of surgical intervention, is the cessation or severe curtailment of almost all physical activities likely to give rise to torsional or compressional stresses to the spinal cord. In practical terms, due to the pervading effect of the spinal anatomy on all but the most sedentary and isolated of physical activities, almost complete immobility must be imposed to insure providing an injured spinal area sufficient opportunity to heal. In this context, the term "injury" relates not only to actual compression and torsional injuries to the various anatomical structures of the spinal cord and related neurophysiology, but also to general musculature strains to the large muscle groups interacting with various anatomical regions of the spinal cord.

The human spinal column is a major component of the skeletal system of thirty-three bones comprising seven cervical, twelve thoracic, and five lumbar vertebrae, with the latter merging endwardly into the five fused sacral and the four fused coccyx vertebrae. The twenty-four individual vertebrae have various bony projections with one projection, directed outward from the back of the spine, known as the spinous process. This spinous process of each vertebra can be felt along the back as hard knobs. The individual vertebrae are connected and supported by various cartilages, muscles and ligaments which allow flexibility for bending and twisting of the torso. Between each vertebra is an intervertebral disc which functions to cushion and separate each vertebra, helping to prevent compression of the peripheral spinal nerves branching off from the spinal cord and housed within the spinal column. Displacement of one or more of the individual vertebrae from its normal position can create pressure against the spinal nerves, most often resulting in pain, frequently severe in intensity. Such displacement is often the result of unequal tension of the muscles supporting the spinal column, causing one or more of the individual vertebrae to be pulled out of alignment with the rest. This unequal tension of the muscles can be caused from a variety of factors, not all of which are physical. These include over-exertion, uneven muscular stress, emotional tension and direct physical trauma.

A great majority of back pain experienced by the general public occurs in the lower portion of the back generally referred to as the lumbar region, or spinal segments L-3 through S-1, specifically. Once the affected vertebrae of this region are re-aligned, the pressure exerted against the nerves can be alleviated, resulting in reduction or elimination of pain.

As a whole, back injuries are a very costly health problem for industry, as measured in terms of lost productivity. Some estimates place the total cost of back injuries to industry in the United States at approximately one hundred billion dollars per year. It is estimated that each year nearly half a million workers are permanently sidelined by back injuries. Lower back pain and back injuries account for nearly forty percent of all work days missed, resulting in over 93 million lost work days per year. Many lower back injuries and much lower back pain result from improper lifting mechanics or techniques. Thus, many of these injuries that occur can be prevented by proper lifting techniques; however, even with training in proper techniques, many workers fail to use such techniques and become injured.

The lumbar spine can be injured in essentially two ways—namely, excessive compression or excessive torsion. If the former occurs, the most common result is a damaged vertebral endplate. The preferable remedy for such injury is rest, or a near-complete avoidance of any physical activity likely to place stress on the spinal column. Corrective surgery is rarely required, as is typical of the vast majority of day-to-day back injuries.

If excessive torsion or twisting occurs, the most common result is a damaged intervertebral disc. In extreme cases, the nucleus of an injured disc may rupture the annulus of the disc and protrude therethrough. Such a protruded disc, or "slipped disc" as it may colloquially be called, can pinch the spinal nerves causing extreme leg pain, or even paresis or paralysis. Corrective surgery to remove disc protrusions or even entire discs may be required. A series of relatively minor torsional injuries, if not allowed to heal, may result in a significantly weakened disc, which may be susceptible to more serious injury. The lumbar spine is generally more susceptible to injury by torsion than by compression. Continued twisting toward an injured side may aggravate the injury and significantly interfere with the healing process.

Because the human spine is the essential load bearing component in the human skeleton, any injury to the spine almost inevitably causes at least some discomfort, immobility or pain. After an injury to the spine has occurred, it is critical that the spine be given an opportunity to heal itself. Spinal motion in the direction of the injury must be avoided if the injury is not to be aggravated, and given an opportunity to heal. If such opportunity is not provided, an injury may never heal or become severely aggravated, causing increasing discomfort and incapacitation to the affected individual. However, because the spine is in constant everyday use, it is continuously subjected to stresses which may interfere with the healing process. In many instances, short of a significant period of absolute bed rest, or even more drastic, non-surgical measures, a spinal injury may never heal properly.

Due to the alarming frequency of lower-back injuries, and the general economic impact on the productivity and efficiency of both industrial workers and the general populace that results from such conditions, considerable attention has been directed toward the development of devices designed to address the problems associated with lower back pain. In general, these devices can be characterized according to the following categories. First of all, there is a multitude of devices designed to prevent the occurrence of lower back injuries such as support belts and braces for workers engaged in repetitive lifting activities, or for the general populace during occasional lifting or athletic endeavors.

Secondly, there are devices designed to be worn during everyday activities by individuals already exhibiting lower back injury symptoms. These devices, which can often be similar in design to the preventative devices, allow the wearer to engage in activities while, in theory, still removing sufficient stress from the lower back to permit some healing of existing injuries, obviating the need for complete inactivity during the healing process. Lastly, there is a class of devices, generally of a far more complex scope mechanically, that are designed to provide active therapeutic benefit in a clinical setting to the injured user. Mechanical traction devices are exemplary of such devices.

With respect to the first class of devices mentioned above, it has been found that provision of additional support to the backs of workers through the use of belts, braces or wraps can considerably reduce the occurrence of back injuries, perhaps because such devices both provide added support, and encourage and remind workers to use better lifting technique. Such belts, braces or wraps appear to provide support by compressing the tissue around the spine so as to stabilize the lumbar region and prevent substantial lateral motion of the lumbar vertebrae relative to one another which, if left unconstrained, could otherwise occur and cause painful injury. Many of the support belts used in the past were merely widened belts which were tightened to provide counter pressure, and did not promote correct extension of the spine. This type of device is exemplified by the U.S. Pat. No. 4,685,668, issued on a weight lifting belt to T. L. Newlin, Jr. on Aug. 11, 1987. These belts were relatively rigid and too much pressure was applied directly on the spinous processes of the vertebrae, which was especially evident when the wearer bent over, resulting in pain along the spine. Wearing this type of belt for an extended period of time also tended to constrict blood flow and cause skin irritation.

Many of these prior art belts, braces or wraps have also been designed specifically to reinforce proper lifting techniques. When lifting heavy objects, it is preferable to use the legs as much as possible to perform the lift, thus relieving strain from the spine and muscles of the back. To insure that the legs are doing most of the lifting as opposed to the back, the lift should begin with the lifter in a squatting position with the back aligned within 45° of vertical. However, individuals often lift items with the back aligned 45°-90° beyond vertical such that the back bears most of the load during lifting. Many braces incorporate features which make it uncomfortable for a wearer to bend their back more than 45 degrees from vertical, thereby mechanically constraining the wearer from exceeding a degree of alignment of the back associated with proper lifting technique.

Often these devices employ padded regions designed to come in contact with the lumbar region of the spine, providing additional support to that region. Specific examples of belts designed to place various pads against the lumbar region of the wearer's back are shown in U.S. Pat. No. 4,991,573 to Miller in which the principal inventive focus of the device is the specific design of the lumbar pad; U.S. Pat. No. 5,188,586 to Castel et al which discloses a back brace designed to prevent injuries to the lower back and impose proper lifting technique on the wearer by constraining the range of motion during lifting; U.S. Pat. No. 4,768,499 to Kemp discloses a lifting belt with an unpadded lumbar panel, also designed to provide additional support to the abdominal region of the wearer during lifting; and U.S. Pat. No. 5,060,639 to Marcus which also discloses a back support providing additional support to the abdominal region of the wearer, including an embodiment suited for use by expectant mothers in the latter stages of pregnancy.

Numerous examples also exist of braces and belts which utilize a lumbar pad comprising fluid-filled compartments designed to conform to the unique contours of the wearer's back. For example, U.S. Pat. No. 4,622,957, which issued Nov. 18, 1986 to James D. Curlee, discloses a therapeutic corset adapted for the sacrum, lumbar and thoracic regions of the body. The corset includes a padded bladder provided with a duct for introducing fluid. The inflated bladder is disposed next to the user for the purpose of "filling" the unique contours of the sacro-lumbar region of the spine by providing a pressure for comfort to specific areas while controlling the overall stability of the thoracic spinal region. U.S. Pat. No. 4,552,135, which issued Nov. 12, 1985 to Gabor B. Racz, et al, also shows a "Lumbar Belt" with a relatively large rear belt section superimposed over the small of the back, and an air-filled chamber disposed between the small of the back and the belt. U.S. Pat. No. 5,111,807 to Spahn et al. also discloses a back belt with a pressurizable air chamber in the lumbar region pad, along with unique connector means designed to couple the diverse materials of construction of the belt in a manner superior to that of conventional sewing. However, all of these devices, although designed primarily to constrain the range of motion of the wearer to prevent injury, also result in a compression of the lumbar area which can have little or no therapeutic value and, in some instances, can actually result in an increase in the likelihood of the wearer to sustain a compressive-type injury.

In conformance with the second category of back devices described above, braces and belts of various designs are used to support the lumbar region of the spine after it has been injured. An example of such a device is disclosed in U.S. Pat. No. 4,691,696 to Farfan de los Godos which comprises a belt with one or more bracing structures designed to prevent torsional rotation of the wearer's back in the direction of an existing injury, thereby relieving stress from the injured area and providing an opportunity for the injury to heal. Additional support braces exist in the prior art, such as that disclosed in U.S. Pat. No. 5,062,414 to Grim which utilize one or more fluid-filled chambers in the lumbar region of the belt, optionally in conjunction with electrically heated resistive elements designed to warm the injured area. Another example of a brace comprising fluid-filled bladders in a lumbar pad, along with electrically heated resistive elements, is disclosed in U.S Pat. No. 4,702,235 to Hong.

Additionally, there are several well known braces of the wrap-around corset type. Such corset braces wrap around the trunk of the body in the region of the lumbar spine. Such braces, however, are intended to reduce the compressive stress in the lumbar spine or to totally immobilize it. They are thus of limited value in the treatment of torsional or twisting injuries. In addition, they may be uncomfortable and difficult to fit to larger persons. Moreover, the highly constraining corset design imparts almost complete immobility to the torso of the wearer and is, therefore, ill-suited for use while pursuing day-to-day activities. Rigidly reinforced or rigid frame back braces are also well known. Such braces, however, also completely immobilize the entire spine. A patient using such a brace is rendered essentially disabled because he cannot move his spine in any way.

According to the third category of back devices described above, there are a number of braces and other such devices which are designed to provide active therapeutic benefit and to promote healing of the injured area. Generally, these devices can range from full scale clinical appliances in the form of tables, chairs or other like structures, to belts and slings designed to be used in conjunction with large appliances. In theory, these devices function by suspending the weight of the affected patient in a manner that almost totally removes all gravitational stresses from the affected area of the spine. Thus, in contrast to the second category of devices described above, traction apparati do far more than merely constrain the movement of the affected region of the body. Generally, they are part of an aggressive, non-surgical or post-surgical regimen designed to keep the spine free from torsional and compressive forces, thus allowing the injured area to heal as rapidly and effectively as possible. The major drawback of most tractional therapies is that, due to the complexity of the apparatus and the need for substantial intervention by an appropriately trained health care professional to assure proper therapeutic use and optimal benefit, they are suited only for use in controlled, clinical settings. The time that a patient spends in a normal traction device must be dedicated time during which the patient is incapable of participating in any other activities.

An example of an orthopedic lumbar traction brace used in conjunction with traction appliances is disclosed in U.S. Pat. No. 4,269,179 to Burton et al. The brace of the Burton et al patent is designed to be attached to the lower rib cage of the patient. The patient, while wearing the device, is suspended through the supporting straps of the device from a multiple-position table which can be adjusted to an optimal angle to achieve a desired amount of gravity traction. Thus, the weight of the patient's upper body is suspended from the brace about the patient's lower rib area and the lumbar region of the spine is relieved of the normal gravitational stresses the patient's body weight would impose even when completely motionless in a standing or sitting position. In conformity with the general comments above, a patient using the brace and traction device disclosed in the Burton et al patent would be precluded from engaging in physical activity of almost any kind.

U.S. Pat. No. 4,991,572 to Chases discloses another type of lumbar traction harness designed in theory to use the principles of gravity traction to relieve stresses from the lumbar spinal region, permitting efficient healing of the affected area. Unlike the device of the Burton et al. patent, the Chases device utilizes an air-inflated bladder to increase the comfort of a patient using the device for traction therapy. This device is basically a traction sling which is adaptable to use in a variety of conformations and patient alignments. This variety of configurations is best illustrated by reference to FIGS. 6-11 of the Chases reference. As disclosed in the reference, the principal advantage of this device is its flexibility of use, being adaptable to a number of patient orientations, unlike the majority of prior art traction tables, such as those used in conjunction with the device of the Burton et al patent. However, as is universally true of this type of therapeutic traction device, the patient undergoing therapy with this device must dedicate the time to participation in the therapy and cannot pursue any normal day-today activities, whether or not employment-related, during therapy.

Thus, each of the categories of back braces described above, although useful, exhibit considerable drawbacks and inefficiencies. The first category of devices, those designed to prevent injury and/or to encourage proper lifting technique, are hampered by a limited efficacy. Furthermore, such devices generally act by compressing the lumbar region in a plurality of dimensions and, aside from restricting motion within a safe range, can possibly lead to an increased likelihood of certain types of back injuries. The second category of devices, those designed to protect an injured wearer while the wearer engages in physical activities, offers not much more protection than those devices designed to decrease the likelihood of initial injury. These latter devices function merely by restricting motion and/or by providing direct support to the lumbar region. Certain devices are also capable of providing heat to the affected area as well. However, both of these initial categories of devices, although they permit the wearer some range of physical activity, can do no more to treat existing injuries than to minimize the likelihood of re-injuring an affected area, or aggravating an existing injury. They are incapable of providing active therapeutic benefits leading to enhanced healing of injuries of the spinal region. Despite whatever other utility these devices may display, the inability to actively promote healing is a significant drawback to these types of devices.

The last category of devices, those exemplified by various designs of traction devices, offer the one significant advantage that the previous two types of devices are incapable of providing—active promotion of healing. However, even these devices suffer from a significant limitation. While undergoing therapy with these devices, the patient is totally incapable of pursuing any other type of physical activity. In this manner, although some productivity gains could be realized through optimizing the healing process and, consequently, minimizing the time away from work and other productive endeavors, the time spent in traction therapy is time that is unavailable for productive activity. Accordingly, any device that is adaptable to everyday use and permits the wearer to pursue day-to-day activities, yet also provides some protection to the spine as it is healing, would be advantageous. Even more advantageous would be a device that would not only protect the injured spine, allowing it to heal, but also could provide active therapeutic benefit to the patient, while still allowing the patient to pursue a reasonably full, everyday life. Until the disclosure contained herein of the present invention, this has been impossible to achieve through use of the prior art devices. Now, the present invention provides a lumbar brace that is suitable for everyday use; provides protection against injury and aggravation of existing injury; and provides the type of active therapeutic benefit in the healing of spine-related injuries that was previously possible only through full scale clinical appliances. All of this, as well as additional benefits, will be apparent from the detailed description of the invention provided below.

DETAILED DESCRIPTION OF THE PREFERRED EMBODIMENTS

Figure 1:
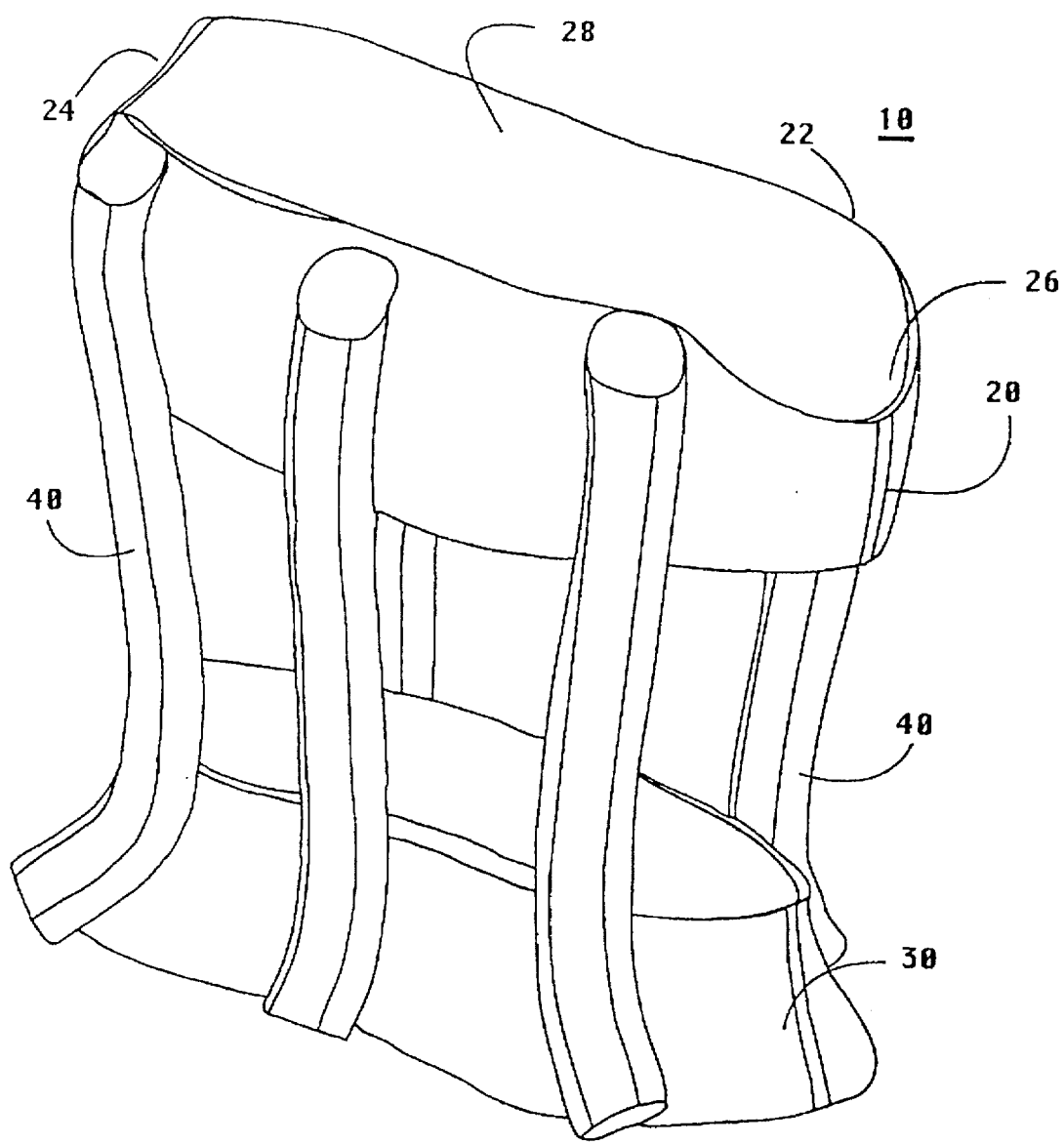
FIG. 1 provides a generalized perspective illustration of an embodiment of the inflatable lumbar traction vest of the invention.

Referring now to FIG. 1, there is depicted at 10 a generalized perspective illustration of an embodiment of the inflatable lumbar traction vest of the invention, presented with a level of detail sufficient to inform the skilled practitioner of the concept and the practice of the invention. As can be seen in FIG. 1, the traction vest of the invention 10 is comprised of an upper torso member 20, a belt member 30, and a plurality of individual vertical inflatable support members 40.

As depicted in FIG. 1, the embodiment of the present invention provides a generalized level of detail. The upper torso member 20 is depicted as a unit of one piece construction. In practice, there are a variety of constructions that are functional for the upper torso member 20. To one of ordinary skill in the appropriate area of art, it will be apparent that the choice of which of these various methods of construction are utilized to prepare an embodiment of the present invention will be determined by such factors as available materials, cost, durability, comfort, and the like. Perhaps the simplest method of construction for the upper torso member 20 would be to utilize an elasticized material such as would be used in the fabrication of support undergarments.

As is depicted in FIG. 1, the upper torso member has a top edge 22. The contour followed by the top edge 22 is designed to allow the arms of the wearer to extend comfortably above the upper torso member 20. Toward this end, the upper torso member has a right arm access contour 24, and a left arm access contour 26. If a one-piece unitary construction is utilized for the upper torso member 20, then it is anticipated that the lumbar traction vest of the invention would be donned by the wearer by first slipping the arms and head through the upper torso member 20.

A key consideration to weigh in the selection of design materials and in the actual construction of the upper torso member would be the ultimate comfort of the wearer. This comfort would depend to a large extent on the degree of flexibility of the material of construction of the upper torso member 20, as well as the size of the wearer and the actual fabric of construction. It will be recognized that certain materials of construction, such as plastics and the like, would have lower degrees of flexibility and also could prove to be uncomfortable to the wearer in that they would make it difficult for circulation of air between the inside surface 28 of the upper torso member, and the outer surface of the wearer. Of additional consideration in this regard would be the ability of the material of construction to "breathe" sufficiently to allow the passage of moisture from the skin of the wearer to the atmosphere. With this in mind, materials such as plastics would be less suitable than the type of flexible fabric material normally associated with elasticized support undergarments.

Alternatively, as would be recognized by one of skill in the art, a variety of other designs could be used for the construction of the upper torso member. The upper torso member could be constructed of a semi-flexible material, or even a canvas or nylon of sufficient strength, with an opening disposed either to the front, to the rear, or to either side of the torso, wherein the opening may be secured by adjustable means such as laces, buckles, or even Velcro™ type-closures. With a construction requiring closure in such fashion, the wearer could don the vest in a simpler manner, one that is similar to donning a regular garment. Construction of the upper torso member 20 requiring closure in this manner would also provide additional means to adjust the fit of the vest to the wearer, if necessary. As will be apparent from the description below, the fit of the upper torso member can be critical in that it is an essential element in the transfer of gravitational forces to the proper structural elements of the vest.

The lower belt member 30 is depicted in FIG. 1 in a single unitary construction. Although it is theoretically possible, utilizing materials of sufficient flexibility and stretch, to so construct the lower belt member, preferably it is advisable to construct the lower belt member along the lines of a conventional front-buckling belt. Once again, both the specifics of construction, as well as the material choices, for the lower belt member 30 depend upon a number of practical factors, such as availability, comfort, cost, and the like. It is contemplated that the lower belt member can most practically be constructed from readily available weight-supporting belts such as those utilized in conjunction with external frame backpacks.

As used with those devices, these types of belts are designed to distribute the bulk of the weight forces of the whole apparatus to a portion of the wearer's body, namely the hips, that is best suited to bear that load. These types of belts are typically worn fairly low on the hips and are tightened snugly thereto to ensure that the distribution of forces is accomplished in an efficient and effective manner. In a like fashion, the lower belt 30 of the lumbar traction vest 10 is designed to receive the bulk of the weight-related forces acting on the vest 10, and transfer those forces to the wearer's hips. It should be recognized here that the phenomenon that occurs through this weight transfer mechanism is essentially the same phenomenon that produces the therapeutic effect of large traction appliances used in clinical settings. In the practice of the present invention, the weight of the upper body of the wearer is essentially hung from the upper torso member 20, and distributed through the inflatable support members 40 to the lower belt member 30. Thus, the weight forces normally experienced by the lumbar region of the spine are instead carried by the hips of the wearer, leaving the lumbar vertebrae free from compressional and torsional stress and, therefore, allowing injured spinal anatomy a chance to heal properly. Once again, this is the same basic concept that is in operation in the use of full-sized mechanical traction appliances such as those of the prior art discussed above.

Where a principal advantage to the present invention lies is in the fact that, unlike traction devices, the vest is light enough and comfortable enough so that the wearer may use the vest for extended periods of time without experiencing appreciable discomfort. Even more important, the construction of the lumbar traction vest 10 is such that the vest possesses sufficient flexibility to allow the wearer to engage in a reasonable range of physical activity, all without imparting undue stress to the injured spinal region. Key elements in accomplishing the transfer of forces to the lower belt member, and at the same time maintaining flexibility of the vest that permits the wearer to engage in moderate levels of physical activity, are the vertical inflatable support members 40. As illustrated in FIG. 1, the inflatable lumbar traction vest 10 is shown with five vertical inflatable support members 40. Although the exact number of support members 40 incorporated into the design of the traction vest 10 is important, it is not critical to achieving the desired function of the vest that there be five vertical members. The inventor considers five vertical members to be an ideal, although not essential, configuration. Such a number of support members 40 provides sufficient support between the upper and lower members of the vest, as well as allowing for sufficient flexibility to permit the wearer a reasonable range of activities while wearing the vest.

It will be recognized by one of appropriate skill that the actual number of vertical support members 40 can be fewer than five, or more than five. Generally speaking, it would be undesirable for the number of inflatable support members to be less than four. With a configuration of four vertical support members, these would preferably be distributed with two in the front of the vest and two in the rear of the vest. It is also possible to have more than five members, such as six, where the plurality of vertical inflatable support members 40 would be distributed equally between the front and back portions of the vest 10. As is exemplified by the embodiment illustrated in FIG. 1, for an odd number of vertical support members 40, the extra or "odd" member is preferably distributed at the front of the vest 10 although such distribution is not an absolute requirement. There are a variety of practical reasons behind this preference, among them being that the extra member in the front of the vest 10 can provide additional protection against the wearer exceeding an appropriate range of motion during physical activity and thus transferring harmful stresses to the affected area of the lumbar spine. It is also contemplated that a greater number of vertical support members 40 may be desirable for some applications where greater levels of constraint of movement may be preferable, such as those designed to correct deviations in spinal conformation typical of conditions such as spina bifida.

There also exists a practical limit on the upper number of vertical support members 40 used in the vest. A significant, advantageous feature of the vertical orientation of the inflatable support members of the invention lies in the fact that such an orientation leads directly to the mechanical distribution of forces within the vest 10. Alternative orientations of inflatable members, for example in a horizontal orientation or in a torroidal configuration, could lead directly to spinal compression, as opposed to spinal support or re-distribution of forces acting on the spine. Thus, inflation of a horizontally-oriented bladder system could result in the same type of effect evidenced with prior art corset-type braces discussed above which can significantly immobilize the wearer. It is contemplated that a similar effect could result from the use of too many vertical inflatable members in the design of the vest of the present invention.

Figure 2:
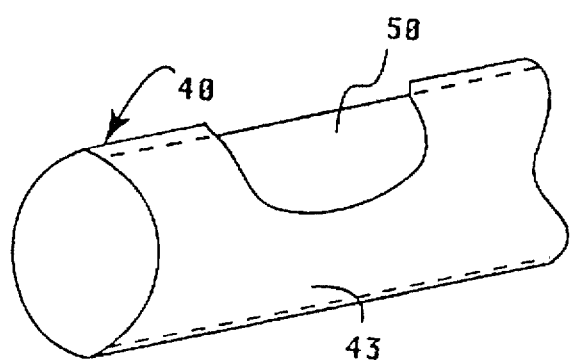
FIG. 2 illustrates a partial cut-out perspective of the vertical support members of an embodiment of the invention.

As shown in FIG. 1, the plurality of vertical support members 40 are of approximately equal diameter, which diameter is preferably 1 inch or, more preferably, about ½ inch, although individual members may have a slightly different conformation depending upon their relative positions on the vest 10. Essential to the effective function of these vertical support members are the air-inflatable bladders 50, as illustrated in FIG. 2 in partial cut-away section. The embodiment of the present invention illustrated in FIG. 2 contemplates but a single inflatable bladder 50 present in each of the vertical support members 40. However, it will be recognized that it is possible for a plurality of essentially cylindrical bladders to be utilized in each vertical support member 40, each of the plurality in fluid communication so that a single source of air or other suitable gas would be capable of inflating the plurality of bladders 50 in a single vertical support member 40.

The bladders 50 may be constructed of a variety of materials possessing the desirable characteristics of flexibility and strength. However, it is contemplated that the preferable material of construction of the bladders 50 be latex due to the ease of fabrication possible with such material. Such material can be fabricated into appropriate bladders by specialty manufacturers such as North American Latex of Sullivan, Ind. As contemplated by this embodiment of the present invention, the diameter of the bladders 50 controls the diameter of the inflatable support members 40. Given the use of latex as the material of the bladders, a maximum practical diameter of the cylindrically-shaped bladders would be about 1 inch or less. Latex bladders of this diameter would be safely capable of inflation to a maximum pressure of approximately 20 lbs/in$^2$. However, it is necessary to inflate the bladders 50 only to a pressure in the range of 6–12 lbs/in$^2$ to achieve the desired mechanical characteristics of the vertical support members, at least for the majority of contemplated applications of the lumbar traction vest 10. Variation in the range of inflation pressure can also be achieved through selection of the material of construction of the bladders, as well as the number of vertical support members 40 utilized on the vest, and the number of bladder segments within any one support member 40. In the context of inflation pressure, it is important to remember that it is desired to retain a sufficient degree of flexibility in the fully inflated vest so that the wearer will not be so constrained in movement as to be practically immobile. For the majority of applications contemplated for the vest 10, it will remain preferable for the wearer to be free to engage in a reasonable degree of physical movement while wearing the vest. This is where selection of the material of construction of the bladders 50 becomes important; latex is particularly advantageous in that it is capable of maintaining sufficient flexibility when inflated to the desired level of pressure.

Depending upon the choice of material of construction for both the bladder and the outer portion 43 of the vertical support members, it may be necessary to incorporate additional support means into the bladders and/or the vertical support members. These additional support means serve the purpose of importing additional stiffness, and therefore support, to the vertical support means. Suitable material of construction for these additional support means may be wood, plastic or even metal. In the case of plastic, the individual additional support means may then be advantageously fabricated to a contour that matches the wearer's body contours.

Alternatively, for an application where it is desirable for the inflatable vest of the present invention to impose mechanical restraints on anatomical structures of the wearer's spinal region, as would the case where the vest was utilized to import a construction to a mis-aligned spine typical of the condition of spina bifida, the additional support means may be constructed of a less flexible, stiffer material, preferably pre-molded to the desired conformation.

An additional consideration in the function of the vertical support members is the material of construction of the outer portion 43 of the members 40. The specific material of construction chosen here is less critical than the choice of bladder material and will typically be driven by cost, availability and, to a lesser extent, comfort. It is possible for the outer portion of the vertical members to be constructed from such materials as canvas or nylon, although nylon would be preferable due to weight considerations. An additional function of the outer portion 43 of the vertical members 40 is to constrain the inflation of the bladders 50 and to physically limit the expansion of the flexible bladders upon inflation.

Figure 3:
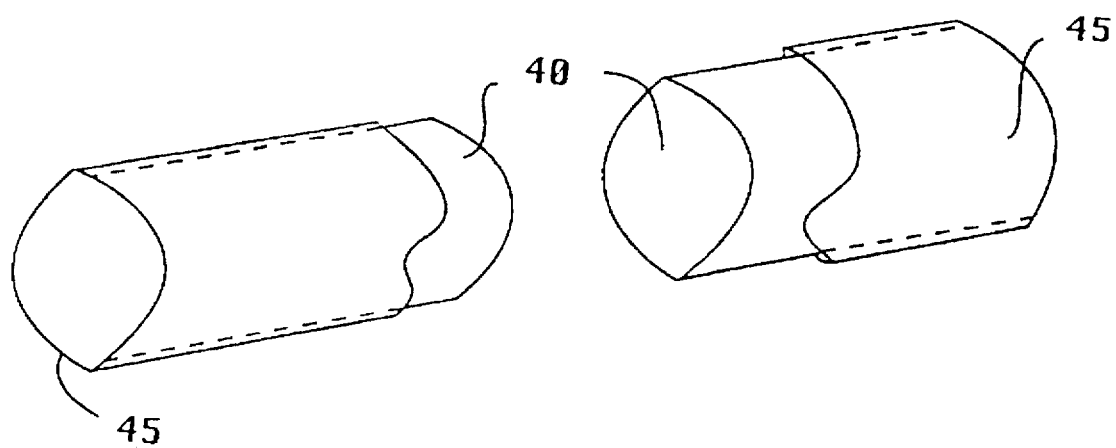
FIG. 3 provides an illustration of the vertical support members of an embodiment of the invention further illustrating the receiving cup members affixed to the upper and lower members of the vest.

The vertical support members 40 can be mechanically affixed to the upper torso member 20 and the lower belt member by a variety of means. As illustrated in FIG. 3, each end of the vertical support members is placed in receiving cup members 45 permanently affixed to the vertical members of the vest by a variety of means, such as gluing, sewing, and the like. It is also contemplated that the vertical support members can be directly coupled to the horizontal members of the vest 20 without the use of receiving cup members. Again, there are a variety of design and manufacturing considerations that will dictate the specific means of coupling the vertical support members 40 to the upper torso member 20 and the lower belt member 30. Such choices should be well within the experience of a practitioner of appropriate level of skill in the art.

Figure 4:
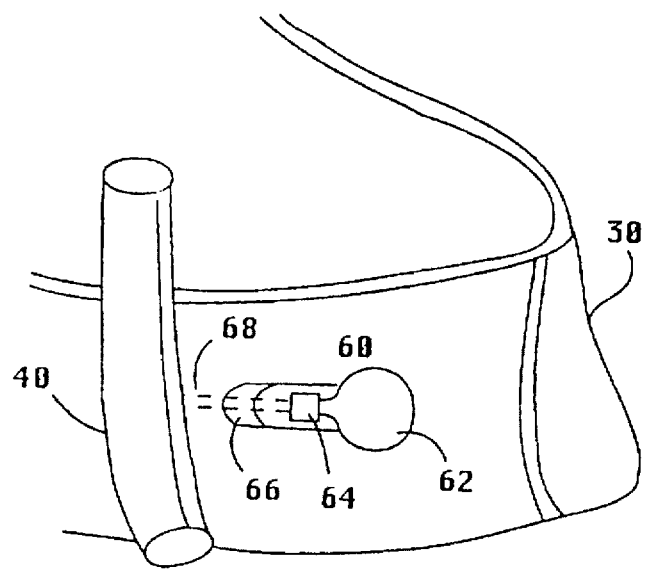
FIG. 4 provides in perspective an illustration of inflation means for the vest of an embodiment of the invention.

Inflation of the bladders 50 disposed inside the vertical support members may be accomplished by a variety of means, as would be apparent to a skilled practitioner. One of these is illustrated in FIG. 4. Illustrated therein is a hand pump mechanism shown generally at 60. This pump mechanism 60 comprises a removable pumping bulb 62, a pressure fitting 64, and a bladder access port 66. The bladder access port is, in turn, in fluid communication with a bladder channel 68 through which air is forced by hand squeezing of the pumping bulb 62. Such pressure fitting could be a common Schraeder-type valve typically found on bicycle and car tires. With such a fitting, pressure inside the bladders could be relieved through the simple act of depressing the central valve stem in the fitting. Alternatively, a Velcro™ type-closure (not shown) could be provided to cover the non-removable components of the inflation mechanism 60 when not in use.

It is also contemplated that each of a plurality of inflation mechanisms 60 be in fluid communication with each of a plurality of bladders distributed throughout the vertical support members. In this fashion, it would be possible to selectively tailor the inflation pressure within the vest 10 to provide lesser pressure in some regions of the vest, and greater pressure in others. It is contemplated that this type of custom adjustment of the inflatable bladder system of the vest 10 could be achieved to result in whatever degree of motion would be desired for a particular activity contemplated for the wearer. The number and distribution of such separate bladders within the bladder system of the vest would be limited by such practical considerations as the complexity of manufacture, the resulting costs of multiple-component systems, and the specific applications of the vest.

Figure 5:
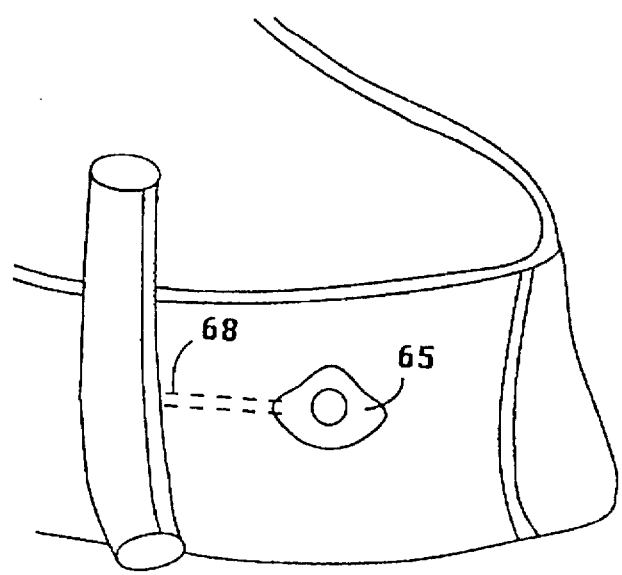
FIG. 5 provides an illustration of an alternative embodiment of the inflation means of the present invention.

It is also contemplated that alternative mechanisms be utilized for pressurizing the bladder system of the vest. One of these is illustrated in FIG. 5. The mechanism contemplated here is a completely enclosed pump means 65 which is activated by downward pressure of the wearer's thumb on the convex surface of the pump means. Such systems find frequent use in inflatable sporting apparati. Usually associated with such inflation means are hand-operated pressure release valves (not shown) so that the air pressure within the bladders 50 may be relieved to facilitate the removal of the vest 10 from the wearer.

An alternative means for inflation of the bladder system within the vest is possible in conjunction with an important anticipated application of the lumbar traction vest of the invention. Currently, long haul truck drivers are frequently beset with a variety of lower back ailments stemming from the repetitive bouncing and jarring such drivers experience during long hours of driving. Such conditions are often aggravated by the fact that these drivers frequently must go directly from long hours of driving, with accompanying stresses applied to the lower spinal regions, to unloading of the transported goods from their trucks at a destination. If such lifting is not preceded by appropriate stretching of the lower back regions and warming up of the muscles involved in heavy lifting, then the chances of injury to the lower back become much higher. If the driver does not follow proper lifting technique, then the situation is exacerbated. The vest of the present invention provides an ideal means for such long-haul drivers to avoid injury to their lower backs, as well as aggravation of existing injuries during long hours behind the wheel. A significant advantage of the present invention, as described above, is that it is capable of being worn during a wide range of physical activity. Furthermore, it is comfortable enough to be worn for relatively long periods of time so that, even if the degree of therapeutic effect does not rise to the level associated with clinical traction appliances, the overall effect of the use of the vest of the invention can match or exceed that of the large appliances. Such characteristics make the vest of the present invention ideally suited for use by long haul truckers.

Most large tractor/trailer combinations employ a compressed air apparatus associated with the brake system of the truck. It is relatively easy to utilize a means to tap into that source of pressurized air and extend a hose and coupling means into the cabin of the truck for inflation of the bladders of the vest while the wearer is driving the truck. Connection to the compressed air system of the truck can be achieved by mechanical hose coupling devices such as a luer lock fitting. Thus, the wearer can inflate the vest while driving to a level of pressure that is personally comfortable, arrive at the scheduled destination, further adjust the inflation level using the air hose means, and then immediately upon parking the truck, begin to unload cargo while still wearing the vest of the invention, and after uncoupling from the air hose means.

Regardless of what mechanical means is used to bring pressurizing gases to the bladder system of the vest, the present invention contemplates the use of a check valve associated with each separate bladder within the vest so that there is no chance of an over-inflation occurring during wearing of the vest. Valves of this nature are well-known in the art. Typically, such valves can be selected or set to match the maximum rated inflation pressures of the individual bladders. Thus, when the pressure rises to the safe limit of a bladder, either during inflation or during use, the check valve will activate to relieve the buildup of pressure before damage can occur to the vest, or injury to the wearer.

Although the above description of preferred embodiments of the present invention clearly illustrates the concepts and practice of the invention, it will be recognized by one of skill in the art that the present invention may assume a plurality of embodiments. In recognition of this, the description provided above is illustrative only and not intruded as a limitation of what the application considers to be his invention, which invention is limited only by the metes and bounds of the claims set forth below.

What is claimed is:

1. An inflatable lumbar traction device, comprising:
   an upper torso member;
   a lower belt member for affixing about a wearer's hips; and
   a plurality of support members, each fixedly attached at a first end to the upper torso member and at a second end to the lower belt member;
   wherein the plurality of support members are distributed both posteriorly and anteriorly to the upper torso member and the lower belt member;
   further wherein each of the plurality of support members contains therein at least one inflatable bladder;
   further wherein the at least one inflatable bladder of each of the plurality of support members is in fluid communication with an inflation device;
   further wherein each support member is spaced from an adjacent support member by a predetermined distance to provide overall flexibility to the device.

2. The inflatable lumbar traction device of claim 1, wherein the plurality of support members comprises five support members.

3. The inflatable lumbar traction device of claim 1, wherein the plurality of support members comprises four support members.

4. The inflatable lumbar traction device of claim 1, wherein the inflation device comprises a manual pump.

5. The inflatable lumbar traction device of claim 1, wherein the inflation device comprises a compressed-fluid system.

6. The inflatable lumbar traction device of claim 1, wherein each support member is free of contact with any adjacent support member.

7. The inflatable lumbar traction device of claim 1, wherein the plurality of support members comprises a plurality of substantially vertical support members.

8. The inflatable lumbar traction device of claim 1, wherein each of the support members is disposed substantially transversely to both the upper torso member and the lower belt member.

9. An inflatable lumbar traction device having an anterior portion and a posterior portion and being designed to be worn on the body of a wearer, the body having a torso extending generally from the wearer's hips and rib cage to the wearer's arms, the inflatable lumbar traction device being in fluid communication with an inflation device, the inflatable lumbar traction device comprising:

an upper torso member for being disposed proximate the wearer's rib cage;

a lower belt member for being disposed proximate the wearer's hips;

a plurality of inflatable support members collectively being distributed on the posterior portion and on the anterior portion of the inflatable lumbar traction device, each of the plurality of inflatable support members having a first portion operably coupled to the upper torso member and a second portion operably coupled to the lower belt member; and a plurality of fluid access ports respectively operably coupled to the plurality of support members, the plurality of fluid access ports being in fluid communication with the inflation device;

wherein each support member is spaced from an adjacent support member by a predetermined distance to provide overall flexibility to the device.

10. The inflatable lumbar traction device of claim 9, wherein the upper torso member includes arm access contours for accommodating generally unrestricted movement of the wearer's arms.

11. The inflatable lumbar traction device of claim 9, wherein the upper torso member is formed of a flexible fabric material.

12. The inflatable lumbar traction device of claim 9, wherein the lower belt member is front-fastening and comprises a fastener disposed anteriorly to the lower belt member.

13. The inflatable lumbar traction device of claim 9, wherein the plurality of inflatable support members comprises at least four inflatable support members, at least two of said inflatable support members being disposed anteriorly of the upper torso member and lower belt member and at least two of said inflatable support members being disposed posteriorly of the upper torso member and lower belt member.

14. The inflatable lumbar traction device of claim 9, wherein the plurality of inflatable support members comprises five inflatable support members, two of said inflatable support members being disposed anteriorly of the upper torso member and the lower belt member and three of said inflatable support members being disposed posteriorly of the upper torso member and the lower belt member.

15. The inflatable lumbar traction device of claim 9, wherein each of the inflatable support members comprises at least one bladder.

16. The inflatable lumber traction device of claim 15, wherein each bladder is formed of an elastic material.

17. The inflatable lumber traction device of claim 15, wherein each bladder comprises a stiffening support formed integral therewith for increasing the stiffness of the corresponding inflatable support member.

18. The inflatable lumbar traction device of claim 15, wherein each bladder is operably, fluidly coupled to the inflation device and is inflatable thereby to a maximum of twenty pounds per square inch.

19. The inflatable lumbar traction device of claim 15, wherein each bladder is operably, fluidly coupled to the inflation device and is inflatable thereby to a maximum of between six and twelve pounds per square inch.

20. The inflatable lumbar traction device of claim 9, wherein each of the inflatable support members is disposed substantially transversely to both the upper torso member and the lower belt member.

21. The inflatable lumbar traction device of claim 9 wherein each of the inflatable support members includes outer sleeve material, said outer sleeve material acting to limit radial expansion of the inflatable support member when the inflatable support member is inflated.

22. The inflatable lumbar traction device of claim 21, wherein the outer sleeve material is formed of fabric.

23. The inflatable lumbar traction device of claim 22, wherein the fabric of the outer sleeve material is selected from a group consisting of canvas and nylon.

24. The inflatable lumbar traction device of claim 9, wherein each inflatable support member comprises a check valve for substantially preventing overinflation.

25. The inflatable lumbar traction device of claim 9, wherein the plurality of inflatable support members comprises a plurality of substantially vertical inflatable support members.

26. The inflatable lumbar traction device of claim 9, wherein each support member is free of contact with any adjacent support member.

\* \* \* \* \*

UNITED STATES PATENT AND TRADEMARK OFFICE
CERTIFICATE OF CORRECTION

PATENT NO. : 5,704,904
DATED : January 6, 1998
INVENTOR(S) : Dunfee

It is certified that error appears in the above-identified patent and that said Letters Patent is hereby corrected as shown below:

In the title, delete "LUMBER" and insert --LUMBAR--.

Column 1, line 1, delete "LUMBER" and insert --LUMBAR--.

Column 1, line 13, delete "saplens" and insert --sapiens--.

Column 1, line 66, delete "L-3" and insert --L-3--.

Column 1, line 67, delete "S-1" and insert --S-1--.

Column 3, line 47, delete "45 degrees" and insert --45°--.

Column 3, line 57, delete "et al" and insert --et al.--.

Column 4, line 14, delete "et al," and insert --et al.--.

Column 5, lines 22, 34 and 51, delete "et al" and insert --et al.--.

Column 5, line 55, delete "today" and insert --to-day--.

UNITED STATES PATENT AND TRADEMARK OFFICE
CERTIFICATE OF CORRECTION

PATENT NO. : 5,704,904
DATED : January 6, 1998
INVENTOR(S) : Dunfee

It is certified that error appears in the above-indentified patent and that said Letters Patent is hereby corrected as shown below:

Column 14, lines 18 and 20, delete "lumber" and insert --lumbar--.

Signed and Sealed this

Twenty-first Day of July, 1998

Attest:

BRUCE LEHMAN

*Attesting Officer*   *Commissioner of Patents and Trademarks*

UNITED STATES PATENT AND TRADEMARK OFFICE
CERTIFICATE OF CORRECTION

Patent No.: 5,704,904
Dated: January 6, 1998
Inventor(s): Dunfee

It is certified that errors appear in the above-identified patent and that said Letters Patent is hereby corrected as shown below:

Face Page [54] delete "INFLATABLE LUMBER TRACTION VEST", and insert --INFLATABLE LUMBAR TRACTION VEST--.

Signed and Sealed this

First Day of May, 2001

Attest:

NICHOLAS P. GODICI

Attesting Officer     Acting Director of the United States Patent and Trademark Office